(12) United States Patent
Gottschalk et al.

(10) Patent No.: US 6,218,195 B1
(45) Date of Patent: Apr. 17, 2001

(54) **ELISA SERODIAGNOSIS OF PIG *PLEUROPNEUMONIA* SEROTYPES 1, 9, AND 11**

(75) Inventors: Marcelo Gottschalk, St-Charles-sur-Richelieu; Daniel Dubreuil, Montréal; Réal Lallier, Ste-Hyacinthe, all of (CA)

(73) Assignee: Universite de Montreal, Quebec (CA)

( * ) Notice: Subject to any disclaimer, the term of this patent is extended or adjusted under 35 U.S.C. 154(b) by 0 days.

(21) Appl. No.: 09/371,218

(22) Filed: Aug. 10, 1999

Related U.S. Application Data (63) Continuation-in-part of application No. 08/501,489, filed on Jul. 12, 1995, now abandoned.

(51) Int. Cl.$^7$ ................................................. G01N 33/543
(52) U.S. Cl. ................................ 436/518; 435/4; 435/7.2; 435/7.1; 435/7.32; 435/7.72; 435/7.9; 435/7.92; 435/975; 536/123.1; 536/127
(58) Field of Search .......................... 424/234.1; 436/518; 435/975, 4, 7.2, 7.1, 7.32, 7.72, 7.9, 7.92; 536/123.1, 127

(56) References Cited

U.S. PATENT DOCUMENTS 4,281,061 * 7/1981 Zuk et al. .

FOREIGN PATENT DOCUMENTS

| 276686 | 7/1992 | (CS) . |
| 02176464 | 7/1990 | (JP) . |

OTHER PUBLICATIONS

Bosse J. et al., 1990, Can J. Vet. Res., 54:427–431.*
Goyette G. et al., 1986, Int. Pig. Ve. Soc. Proc., 9:258.*
Inzana T. and Mathison T., 1987, Infect. Immun., 55:1580–87.*
Mittal K. et al., 1984, Am. J. Vet. Res., 45:715–9.*
Nadeau M. and Higgins R., 1991, Bulletin Epidemiologique, 2:4–5.*
Perry B. et al., 1990, Sero. Immunol. Infect. Dis., 4:299–308.*
Gottschalk M. et al., 1994, Vet. Microbiol., 42:91–104.*
Trottier Y.L. et al., 1992, J. Clin. Microbiol., 30:46–53.*
Radavovici et al. Veterinary Microbiology, Apr. 1994, 39: 219–230.*
Gottschalk et al. Veterinary Microbiology, 1994: 91–104.*
Sibley et al. Analytical Lett. 1993, 26(8): 1623–1634.*
Calbiochem–Novabiochem Corp., #516534.*
Joshi et al, Mol. Immunol., 29/7–8:971–981, 1992.

* cited by examiner

*Primary Examiner*—Jennifer Graser
(74) *Attorney, Agent, or Firm*—Klauber & Jackson (57) ABSTRACT

The present invention relates to an ELISA diagnostic kit for the assay of *A. pleuropneumoniae* serotypes 1, 9 or 11 antibodies in the serum of pigs comprising in separate packaging, at least one of the following: a) a plate or solid support having bound thereto a purified lipopolysaccharide *A. pleuropneumoniae* serotype 1 antigen for a specific binding to anti-*A. pleuropneumoniae* serotypes 1, 9 or 11 antibodies present in the serum of pigs; b) serum from pigs experimentally inoculated with a strain of *A. pleuropneumoniae* serotypes 1 to serve as a positive control; c) pig serum from *A. pleuropneumoniae* free herd to serve as a negative control; and d) a detectably labeled conjugate which bind to pigs antibodies bound to the plate of a).

15 Claims, 1 Drawing Sheet

BL = Blanks
CP = Positive control
CN = Negative control
S1 to S40 = serum to be analyzed

Fig. 1

ELISA SERODIAGNOSIS OF PIG PLEUROPNEUMONIA SEROTYPES 1, 9, AND 11

RELATED APPLICATION

This application is a continuation-in-part of application Ser. No. 08/501,489 filed on Jul. 12, 1995, now abandoned, which is hereby incorporated by reference in its entirety.

BACKGROUND OF THE INVENTION (a) Field of the Invention

The invention relates to kits for the accurate, rapid and sensitive assay of A. pleuropneumoniae serotypes 1, 9 and 11 antibodies in pig serum for swine pleuropneumonia serodiagnosis.

(b) Description of Prior Art

Actinobacillus pleuropneumoniae is known as one of the most pathogenic agents of the respiratory tract of swine. Swine pleuropneumonia is still an important problem in large swine operations, causing serious economic losses in this industry. Since the presence of A. pleuropneumoniae is often unnoticed in chronically infected herds, the identification of carrier animals is a main concern. Following a stressful situation, several clinically fatal cases may arise in a given herd. Infection in swine can be fatal but animals surviving the infection frequently become carriers. Detection of chronically infected carriers is crucial since those animals act as reservoirs of infection. Since the infection is often unnoticed, serology becomes a useful tool for the detection of chronic infection. Several studies indicate that it is possible to control or eliminate the infection in certain herds based on the serological results.

Various serological assays for A. pleuropneumoniae have been described. Among others, the complement fixation test (CFT), the enzyme-linked immunosorbent assay (ELISA); (Goyette G. et al., 1986, *Int. Pig. Vet. Soc. Proc.,* 9:258) and the 2-mercapto-ethanol tube agglutination test (Mittal, K. et al., 1984, *Am. J. Vet. Res.,* 45:715–719) have been used. Out of the different assays, the ELISA is often the most useful since it is faster and easier to perform. On the other hand, up to now, the results obtained suggested the use of a more purified antigenic preparation in order to improve the specificity of the test.

A saline extract of boiled-formalinized whole cells of *A. pleuropneumoniae* (also called crude extract) is presently used, in some laboratories, as the antigen for ELISA serodiagnosis (Goyette G. et al., 1986, *Int. Pig. Vet. Soc. Proc.,* 9:258). Standardization of the assay is complicated as variations are noticed between extracts.

Using different antigen preparations, cross-reactions among serotypes and with other bacterial species were also reported (Bossé, J. et al., 1990, *Can. J. Vet. Res.,* 54:427–431). Although the capsular polysaccharide (CPS) of *A. pleuropneumoniae* has been shown to be responsible for serotype specificity (Inzana, T. and Mathison, T., 1987, *Infect. Immun.,* 55:1580–1587), the difficulty of obtaining pure CPS in large quantity precludes its utilization for serodiagnostic purposes. The CPS were very unstable and were fixed with difficulty to the walls of the polystyrene plate used in the ELISA assay (Perry, B. et al., 1990, *Sero. Immunol. Infect. Dis.,* 4:299–308).

Serology, which is used to identify animals that have developed an immune response to specific pathogens, is an important tool in disease management and prevention of *A. pleuropneumoniae* infection in pigs. The importance of serological testing is further emphasized by the lack of a vaccine that reliably prevents infection. The demand of pigs from *A. pleuropneumoniae* sero-negative herds is increasing, especially from producers whose herds have experienced acute outbreaks of the disease and who have decided to "eradicate" *A. pleuropneumoniae,* buying only sero-negative animals (coming from sero-negative herds) for the replacement. A successful eradication program depends mostly on the accuracy and reliability of the serological tests used to identify *A. pleuropneumoniae* infected pigs. Nevertheless, interpretation of serology should be done cautiously. A test that is not sensitive will not detect all infected herds or animals (false negative results) and one that is not specific will erroneously condemn some non-infected animals (false positive results).

Presently, it is impossible to serologically distinguish the infection caused by strains of *A. pleuropneumoniae* serotype 1 from that caused by strains of *A. pleuropneumoniae* serotype 9 and/or 11. This is due mainly to the O chain from the lipopolysaccharide (LPS), which presents common antigenic determinants. The antigenic specificity of *A. pleuropneumoniae* mainly comes from the capsular polysaccharides, which are not very immunogenic. Purified capsular polysaccharides antigens are very difficult to obtain and, in addition, contamination with non-specific antigen are very common. The distinction between these serotypes (1-9-11) necessitate bacterial isolation. The isolation of the bacteria from chronically infected animals is a time consuming and low sensitive method.

The use of antibiotics is mainly useful to control the mortality, but it has no real benefit on pigs with chronic pleuropneumonia. Treated animals often continue to carry the organism and can be a source of infection for other animals. In addition, an increasing number of strains resistant to different antimicrobials has been observed in the last years in Québec (Nadeau, M. and Higgins, R., 1991, *Bulletin épidémiologique,* 2:4–5).

There are some cross-reactions among serotypes; for example: serotypes 3, 6 and 8, serotypes 1, 9 and 11, and serotypes 7 and 4. In addition, other cross-reactions, which are not found in serotyping, could be observed in serological analysis of chronically infected animals that are continuously challenged with the microorganism. These cross-reactions are usually associated with outer membrane proteins (cell wall proteins, iron-repressible proteins, etc.) and rough lipopolysaccharides. However, it is important to remember that one herd, and even one animal, might be infected with several serotypes simultaneously. In this case, the detected antibodies against different serotypes are probably not cross-reactions, but homologous and specific reactions. This is one of the most important problem to be solved by the use of specific and sensitive serological tests in accordance with the present invention.

Healthy carrier pigs may be responsible for the transmission of the disease. The absence of clinical signs and/or lesions at the slaughter-house does not implicate necessarily the absence of the infection.

Following infection, antibodies can usually be detected in 10–15 days. Some animals will remain serologically positive for a few months, but most will be positive for a long period of time; once more, it will depend on the test used.

The proportion of seropositive sows as well as their titers tended to decrease with age.

Isolation of *A. pleuropneumoniae* from apparently healthy carrier pigs is difficult; it probably should be used as a complement to the serology in conflictive cases.

The development of better serological tests is a necessity because the infection still has an economic impact on the swine industry and the current vaccines are not effective.

To date, there exist no stable kit for the effective serodiagnosis of pig pleuropneumonia in the field.

It would be highly desirable to be provided with a kit for readily determining the presence of antibodies against *A. pleuropneumoniae* serotypes 1, 9 and 11 in a serum sample.

It would be highly desirable to be provided with such an ELISA diagnostic kit for *A. pleuropneumoniae* which could be used for *A. pleuropneumoniae* serodiagnosis while remaining in the field.

SUMMARY OF THE INVENTION

One aim of the present invention is to provide a kit for the accurate, rapid and sensitive assay of antibodies against *A. pleuropneumoniae* serotypes 1, 9 and 11 in a sample.

Another aim of the present invention is to provide an ELISA diagnostic kit for *A. pleuropneumoniae* to be used for *A. pleuropneumoniae* serodiagnosis while remaining in the field. The novelty and originality of the ELISA diagnostic kit of the present invention resides in the particular combination of a novel purification method of the antigen to be used and a novel sensitization and stabilization methods of the plates of the kit.

The kits of the present invention differs from the ELISA method of the prior art for the determination of *A. pleuropneumoniae* antibodies. In the prior art method, the antigen is fixed to the plates in a PBS buffer and the plates are immediately used after the antigen fixation is completed. The prior art method may include a computerized reading protocol for the determination of the antibodies in the samples as described by Trottier, Y. L. et al. (1992, *J. Clin. Microbiol.*, 30:46–53). The kits of the present invention mainly differ in that the antigen is purified using a higher concentration of phenol and the antigen fixation procedure is different. Indeed, the purified antigen is resuspended in a PBS-EDTA buffer which is then added to each well of the plate. After an 18 hour incubation, horseradish peroxidase (HRP) conjugate stabilizing solution (sold by Calbiochem-Novabiochem Corporation, La Jolla, Calif. 92039, U.S.A., catalogue #516534, containing phosphate buffered saline pH 7.2, BSA, 0.1% thimerosal and caprylic acid) is added to each well. The antibodies in the samples are determined visually by adding a chromogen, preferably 3,3',5,5'-tetramethylbenzidine, e.g. TMBlue™ (Biovest Inc., Massachusetts, U.S.A.)(see U.S. Pat. No. 5,013,646, issued May 7, 1991). The kits of the present invention, when compared to the prior art ELISA method, demonstrate a relative sensitivity and a relative specificity of 100%.

In accordance with one embodiment of the present invention there is provided an ELISA diagnostic kit for the assay of *A. pleuropneumoniae* serotypes 1, 9 or 11 antibodies in the serum of pigs comprising in separate packaging, at least one of the following:

a) a plate or solid support having bound thereto a purified lipopolysaccharide *A. pleuropneumoniae* serotype 1 antigen for a specific binding to anti-*A. pleuropneumoniae* serotypes 1, 9 and 11 antibodies present in the serum of pigs;

b) serum from pigs experimentally inoculated with a strain of *A. pleuropneumoniae* serotypes 1 to serve as a positive control;

c) pig serum from a specific pathogen free herd to serve as a negative control; and d) a detectably labeled conjugate which bind to pigs antibodies bound to the plate of a).

The ELISA diagnostic kits of the present invention may further comprise the following:

e) a substrate which allow the visualization of the detectably labeled conjugate.

In accordance with another embodiment of the present invention there is provided a method for the preparation of the kit, which comprises the steps of:

a) purifying lipopolysaccharide *A. pleuropneumoniae* serotype 1 antigen by phenol extraction and centrifugation of said antigen bacterial crude extract;

b) fixing the antigen of step a) to a solid support and stabilizing said fixed antigen;

c) immunizing mammals with a strain of *A. pleuropneumoniae* serotype 1 and collecting serum to serve as positive control sera; and d) collecting sera from *A. pleuropneumoniae* free herds to serve as negative control sera.

In a particular embodiment the HRP conjugate stabilizing solution for stabilizing the antigen contains phosphate buffered saline pH 7.2, 20 mg/ml BSA, 0.1% thimerosal and a saturating amount of caprylic acid.

DETAILED DESCRIPTION OF THE INVENTION

The kits of the present invention are novel in that they allow for a simple and fast testing in the field where the animals are. These kits are sufficiently stable that they have a shelf life of at least 25 weeks. The antigen was purified according to a novel procedure which allows for an increased sensitivity.

Heretofore, once the antigen was bound to the plate, the antigen was unstable. In contrast, the bound antigen stabilized by the HRP conjugate stabilizing solution (sold by Calbiochem-Novabiochem Corporation, La Jolla, Calif. 9203C, U.S.A., catalogue #516534, i.e. phosphate buffered saline pH 7.2, containing BSA, 0.1% thimerosal and caprylic acid) in accordance with the present invention, is stable for a long time. In fact, the antigen remains stable for at least 25 weeks or until use.

The kits o the present invention are based essentially on the particular combination of a novel method of purification of lipopolysaccharide antigen from a reference strain of *A. pleuropneumoniae* serotype 1 antigen and a novel coating and stabilization of the antigen on the surface of the plate. The kit in accordance with the present invention is very specific, sensitive and stable. The test in accordance with the kit of the present invention consists in the determination of the presence or absence of anti-*A. pleuropneumoniae* antibodies in the serum of pigs for the serodiagnosis of *A. pleuropneumoniae* serotypes 1, 9 and 11.

The test essentially consists in the following steps:

a) A plate of 96 wells sensitized with the specific antigen of *A. pleuropneumoniae* serotype 1 is washed with a PBS-Tween™-20 buffer solution.

b) A serum sample of each pigs from the tested herds is distributed in two sensitized wells of step a). During this first incubation, the anti-*A. pleuropneumoniae* serotypes 1, 9 and 11 antibodies, if present in the sera, will bind to the antigen attached to the plate or solid phase bound.

c) The plate is washed to remove from the wells any unbound material. A peroxidase-anti-IgG conjugate is added to each well, preferably obtained from Jackson Immuno Research Laboratories (catalogue #114-035-003). This conjugate binds to any IgG which would have bound to the antigen attached to the plate in step b). If the pig serum did not contain any anti-*A. pleuropneumoniae* serotypes 1, 9 and 11 antibodies, the conjugate will remain free or in suspension and will be eliminated during this washing step.

d) The presence of immobilized peroxidase within the bound conjugate is revealed by the addition of a chromogen substrate TMBLue™ (sold by Transgenic Science Inc., Milford Mass. 01757, U.S.A., catalogue #TM-102). If the conjugate is present, there will be an oxidation reaction and a blue color will appear.

The preferred kit of the present invention comprises the following items:

1 Five 96-well plates (Nunc™, sold by Gibco, Burlington, Ontario, Canada, L7P 1A1) sensitized and stabilized with the purified antigen in accordance with the present invention.

2 Positive control; five vials containing each 0.1 ml of lyophilized serum from pigs experimentally inoculated with a strain of *A. pleuropneumoniae* serotype 1.

3 Negative control; five vials containing each 0.1 ml of lyophilized pig serum from a specific pathogen free herd.

4 Weak positive control; five vials containing each 0.1 ml of lyophilized serum from pigs experimentally inoculated with a strain of *A. pleuropneumoniae* serotype 1.

5 Conjugate; five vials of pig anti-IgG immunoglobulins coupled to peroxidase. Each vial contains 1.2 ml of lyophilized conjugate.

6 TMBLue™; five vials containing each 10 ml of TMBLue™.

Figure 1:
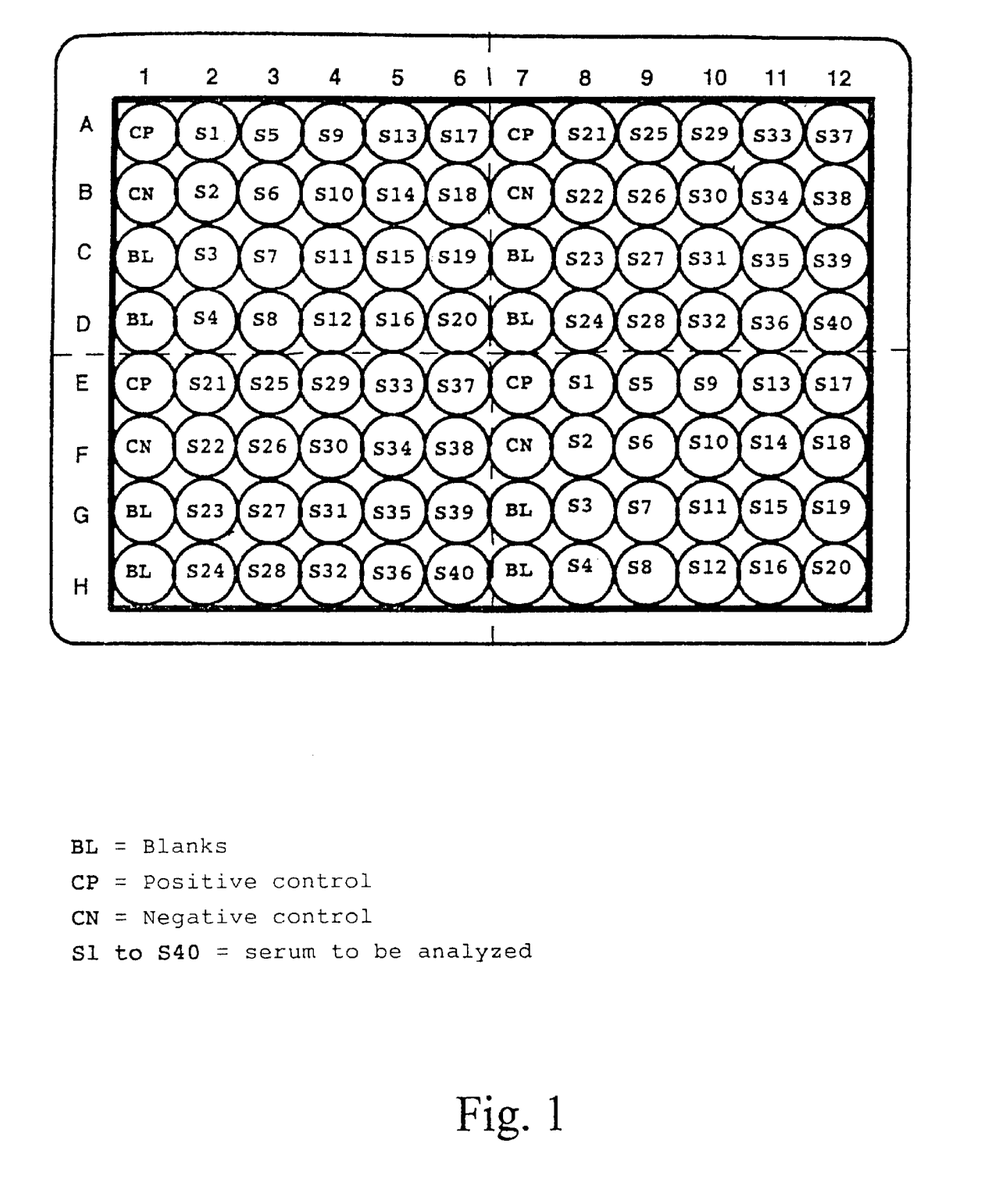
FIG. 1 illustrates the layout of the plate of the preferred kit of the present invention.

FIG. 1 illustrates the layout of the plate of the preferred kit of the present invention, where 40 different sera are analyzed. The wells are identified as follows:

BL=Blanks, PBS-Tween™-20 buffer solution (4 wells)
CP=Positive control, item #2 above (4 wells)
CN=Negative control, item #3 above (4 wells)
CPFA=Weak positive control, item #4 above (4 wells)
S1 to S40=serum to be analyzed, 2 wells for each serum.

Preparation of the PBS-Tween™-20 Buffer Solution

Add the following to 3 L of distilled water,
52.59 g of sodium chloride;
1.47 g of monobasic sodium phosphate;
7.02 g dibasic sodium phosphate;
1.5 ml of Tween™-20.

Mix well until a complete dissolution is achieved. Verify the pH, which should be about 7.30±0.05, if different adjust the pH using dibasic sodium phosphate. This solution has a shelf life of 1 week when kept at 4° C. The buffer solution should always be brought to room temperature before being used in the test.

Bacterial Strain

The international reference strain, Shope 4074 (American Type Culture Collection, 12301 Parklawn Drive, Rockville, Md. 20852 U.S.A., ATCC accession number 27088), of *A. pleuropneumoniae* serotype 1 was used for the antigen production. The strain was kept lyophilized.

Bacterial Culture

The content of a vial was resuspended in one ml of PPLO (Difco Laboratories, Detroit, Mich.) liquid medium and inoculated to exhaustion on a PPLO agar plate. The plate was incubated aerobically for 24 hours at 37° C. A few colonies were resuspended in 5 ml of PPLO liquid medium. PPLO plates were inoculated at confluence with a sterile swab, these plates were then incubated 6 hours at 37° C. After the incubation, the bacterial growth was harvested by adding 3.0 ml of phosphate-buffered saline (PBS, pH 7.4) (Oxoid Ltd., Basingstoke, England) containing 0.5% (vol/vol) of formaldehyde (Fisher scientific, Fair Lawn, N.J.) to each gel plates.

Antigen Purification

The bacterial suspension obtained was placed in a sterile bottle and was allowed to stand overnight at 4° C. The optical density was adjusted to 5.0 with a solution of PBS-0.5% formaldehyde. The suspensions were separated in sterile screw cap vials and boiled 60 min. Then the suspensions were centrifuged at 12,000×g for 30–40 min., 4° C. The supernatants were collected and filtered on a 0.22 $\mu$m pore size filter (Millipore Corp., Bedford, Mass.).

The antigen was purified according to the following procedure.

Preparing the phenol solution by mixing 90 g of phenol crystals with 100 ml of distilled water.

Mixing an equal volume of the phenol solution with an equal volume of the crude extract in Corex™ tubes, mixing by inversion and let stands for 30 min. at room temperature.

Centrifuged at 12,000×g, 4° C. for 30 min.

After the first centrifugation, two phases were obtained with an interface of insoluble material. The aqueous phase was collected with a Pasteur™ pipette and the volume was measured in a graduated cylinder.

Mixing an equal volume of the aqueous phase (first extraction) with an equal volume of the phenol phase in Corex™ tubes, mixing by inversion and let stands for 30 min. at room temperature.

Centrifuged at 12,000×g, 4° C. for 30 min.

The aqueous phase was collected and the volume was measured in a graduated cylinder.

Mixing an equal volume of the aqueous phase (second extraction) with an equal volume of the phenol phase in Corex™ tubes, mixing by inversion and let stands for 30 min. at room temperature.

During this period, prepare the dialysis membrane by soaking in distilled water for a sufficient period of time.

Centrifuged at 12,000×g, 4° C. for 30 min.

The aqueous phase was collected and the volume was measured in a graduated cylinder.

The aqueous phase (third extraction) was dialyzed against 3×12 L of distilled water to remove traces of phenol, do not dialyze for more than 24 hours.

Antisera—Negative Control

Sera from several pigs were obtained at the slaughter from a specific pathogen free herd; the sera were mixed and thimerosal (sold by Sigma, St-Louis, Mo. 14508, U.S.A., catalogue #T-5125) was added to obtain a final concentration of 0.01%. No history of *A. pleuropneumoniae* was ever reported for this herd since at least four years. The sera were tested using the ELISA technique against all the *A. pleuropneumoniae* serotypes by the pleuropneumonia laboratory of the veterinary Medicine Faculty of University of Montreal.

Antisera—Positive Control

The strain *A. pleuropneumoniae* serotype 1 (strain 4074; ATCC 27088) was used for the bacterial production. The content of a vial was resuspended in one ml of PPLO (Difco Laboratories, Detroit, Mich.) liquid medium and inoculated to exhaustion on two PPLO agar plates. The plates were incubated aerobically for 18 hours at 37° C.

The bacterial production for the immunization of pigs was effected according to the following procedure.

Collecting a few colonies isolated with a sterile swab and resuspending them in a PPLO broth.

5 PPLO agar plates were inoculated at confluence with the broth and sterile swabs. One Mueller-Hinton agar plate was inoculated with the remaining broth to serve as a negative control. One PPLO agar plate was inoculated to exhaustion.

These plates were then incubated 18 hours at 37° C. One plate is used for serotyping.

After the incubation, harvesting the bacterial growth by adding 3.0 ml of PBS-0.5% formaldehyde to each plate, and mixed with a hockey stick made of sterile Pasteur™ pipette and recovering the suspension with a pipette.

The bacterial suspension obtained was placed in a sterile bottle, mixed well and incubated 18 hours at room temperature.

The optical density was read at 540 nm and adjusted to 1.0 with a solution of PBS-0.5% formaldehyde.

The solution was kept at 4° C. until usage or for a maximum of one week.

For the immunization, four five-week old piglets were obtained from a specific pathogen free herd. No history of *A. pleuropneumoniae* was ever reported for this herd since at least four years and no pulmonary lesions were observed at the slaughter. At their arrival, the general state of health of the piglets is verified. The piglets are fed on demand with introductory fattening food for pigs (15/30 CO-OP). After a few days of adaptation, a blood sample is taken from each animal. The sera were tested using the ELISA technique against all the *A. pleuropneumoniae* serotypes by the pleuropneumonia laboratory of the Veterinary Medicine Faculty of University of Montreal. The sera were negative for all serotypes.

The pigs were immunized intravenously with 0.5 ml of the bacterial suspension every three weeks and this until the ELISA titer give a value superior or equal to 1.0 with the serum diluted 1/200. The pigs were bled and the serum of each animal was mixed together.

ELISA

For evaluating the efficiency and reliability of the kits of the present invention, two methods of ELISA were used. In the first method, the plates are used immediately after sensitization, the incubation period are of one hour and ABTS (2,2-azino-bis(3-ethylbenzthiazoline-6-sulfonic acid) is used as a chromogen. In the second method, the plates are treated with HRP conjugate stabilizing solution sold by Calbiochem-Novabiochem Corporation, La Jolla, Calif. 92039, U.S.A., catalogue #516534 after sensitization, the incubation period are of 15 min. and TMBLue™ is used as a chromogen.

The ELISA consists in:

1 sensitization of the plates

Diluting in 150 µl of antigen in 75 ml of PBS-EDTA buffer, pH 7.3.

Add 100 µl of antigen to each well.

Seal the plate with an acetate sheet.

Incubate overnight at 4° C.

For the evaluation of the kit, for the stability assays as well as for the visual assays, the plates are treated with HRP conjugate stabilizing solution (sold by Calbiochem-Novabiochem Corporation, La Jolla, Calif. 92039, U.S.A., catalogue #516534, i.e. phosphate buffered saline pH 7.2, containing BSA, 0.1% thimerosal and caprylic acid). The content of the wells are emptied and 100 µl of HRP conjugate stabilizing solution is added to each well. The plates containing the HRP conjugate stabilizing solution are kept at 4° C. until needed.

2 washing of the sensitized plates

Recovering the plate and emptying its content.

Filling each well with PBS-TWEEN™-20 buffer.

Emptying the plate content.

Repeat these steps four times.

Shake off 2–3 times on an absorbing paper to remove any washing solution excess.

3 sera preparation

The sera are diluted 1/200 in PBS-TWEEN™-20 buffer and distributed in the amount of 100 µl to each well.

Gently shake the plate to ensure the distribution of the samples at the bottom of the wells. Cover the plate with an acetate sheet.

Let the plate stand for one hour at room temperature for ELISA using ABTS or for 15 min. between 18° C. and 22° C. for ELISA using TMBLue™.

4 washing of the plate to remove unbound antibodies

Recovering the plate and emptying its content.

Filling each well with PBS-TWEEN™-20 buffer.

Emptying the plate content.

Repeat these steps four times.

Shake off 2–3 times on an absorbing paper to remove any washing solution excess.

5 distribution of conjugate

The conjugate consists in horseradish peroxidase-labeled immunoglobulin G fraction of rabbit antiserum raised against porcine IgG (Jackson Immuno Research Laboratories Inc., catalogue #114-035-003). The conjugate is used at a final dilution of 1/6000. The conjugate is distributed in the amount of 100 µl to each well of the plate.

Gently shake the plate to ensure the distribution of the samples at the bottom of the wells. Cover the plate with an acetate sheet.

Let the plate stand at room temperature for one hour for ELISA using ABTS or for 15 min. for ELISA using TMBLue™.

6 washing of the plate to remove unbound conjugate

Recovering the plate and emptying its content.

Filling each well with PBS-Tween™-20 buffer.

Emptying the plate content.

Repeat these steps four times.

Shake off 2–3 times on an absorbing paper to remove any washing solution excess.

ELISA using ABTS

This was used only to validate the kit of the present invention or to get a spectrophotometer value.

7a preparation and distribution of chromogen

The reaction was visualized using 2 mM $H_2O_2$ and 0.4 mM ABTS (2,2-azino-bis(3-ethylbenzthiazoline-6-sulfonic acid) (Sigma Chemical) in 50 mM citrate solution (pH 4.0). Add 100 µl of this citrate-ABTS solution to each well of the plate.

Gently shake the plate to ensure the distribution of the samples at the bottom of the wells.

Let the plate stand for 30 min. at room temperature (between 18° C. and 22° C.).

8a reading and results interpretation

The optical density was read at 410 nm using an automated plate reader (MR5000™, Dynatech Laboratories Inc.).

The results were calculated according to the following procedure.

1 The values of the eight wells BL (blank) were verified:
  A value inferior to 0.08 indicates a valid test, continue the reading.
  A value superior to 0.08 indicates an invalid test, repeat the test with a new kit or contact the kit manufacturer.

2 The mean values of the negative and positive controls are calculated as follows (see FIG. 1 for identification of wells):

Positive control=((A1+E1+A7+E7)/4)−BL mean

Negative control=((B1+F1+B7+F7)/4)−BL mean

Reproducibility of the Antigen Attachment

The aim of this test series consists in verifying the reproducibility of the antigen bounding at the bottom of the wells of the plate. The variation in the antigen attachment between the wells of a same plate was determined. Each of the 96 wells of each three plates was sensitized with 10 μg of A. pleuropneumoniae serotype 1 antigen, the plates were used immediately after their sensitization according to the above-mentioned ELISA-ABTS procedure. The control sera were distributed in the three plates. The positive control serum was used in 16 wells of each three plates and the negative control serum in 17 wells. Each of the six field controls were distributed in eight wells of each plates. The results are presented in Table 1. The wells which had not receive any serum, the blanks, demonstrated a variation of 10% between the three plates, whereas the wells which received a serum demonstrated variations, interplate and intraplate, inferior to 8%.

TABLE 1

Reproducibility of antigen attachment between wells of a same plate or of different plates

| | Plate #1 | | | Plate #2 | | | Plate #3 | | | Mean of three plates | | |
|---|---|---|---|---|---|---|---|---|---|---|---|---|
| Serum | Mean | Standard deviation | Deviation % | Mean | Standard deviation | Deviation % | Mean | Standard deviation | Deviation % | Mean | Standard deviation | Deviation % |
| B | 0.0554 | 0.0078 | 14.02 | 0.0499 | 0.0065 | 12.97 | 0.0450 | 0.0081 | 17.96 | 0.0501 | 0.0052 | 10.37 |
| CN | 0.1151 | 0.0067 | 5.84 | 0.1206 | 0.0054 | 4.49 | 0.1086 | 0.0046 | 4.24 | 0.1147 | 0.0060 | 5.24 |
| CP | 1.0933 | 0.0424 | 3.87 | 1.1591 | 0.0553 | 4.77 | 1.1420 | 0.0428 | 3.75 | 1.1198 | 0.0347 | 3.10 |
| EP1 | 1.3182 | 0.0423 | 3.21 | 1.3488 | 0.0114 | 0.85 | 1.3978 | 0.0324 | 2.32 | 1.3549 | 0.0402 | 2.97 |
| EP2 | 1.0588 | 0.0766 | 7.23 | 1.0795 | 0.0421 | 3.90 | 1.1157 | 0.0192 | 1.72 | 1.0847 | 0.0288 | 2.65 |
| ENI | 0.3877 | 0.0241 | 6.21 | 0.4295 | 0.0340 | 7.91 | 0.4147 | 0.0165 | 3.98 | 0.4106 | 0.0212 | 5.17 |
| EN2 | 0.1312 | 0.0074 | 5.65 | 0.1367 | 0.0048 | 3.48 | 0.1363 | 0.0038 | 2.81 | 0.1347 | 0.0031 | 2.29 |
| EDI | 0.6470 | 0.0147 | 2.28 | 0.6782 | 0.0239 | 3.52 | 0.6778 | 0.0200 | 2.95 | 0.6677 | 0.0179 | 2.68 |
| ED2 | 0.5372 | 0.0267 | 4.97 | 0.6012 | 0.0185 | 3.07 | 0.6000 | 0.0243 | 4.05 | 0.5794 | 0.0366 | 6.32 |

ELISA Using TMBLue™ in Accordance With the Present Invention 7b preparation and distribution of chromogen Add 100 μl of TMBLue™ to each well of the plate.

Gently shake the plate to ensure the distribution of the samples at the bottom of the wells.

Let the plate stand for 5 min. at room temperature (between 18° C. and 22° C.).

8b reading and results interpretation

The visual reading was effected without any reading instruments as follows:

The results were calculated according to the following procedure.

1 The color of the eight wells BL (blanks) and of the negative controls is verified; it should be colorless.

2 The color of the positive controls is verified; it should be dark blue.

3 The color of the CPFA (weak positive control) is verified; it should be light blue.

4 The answer of each sample should be quantified as follows:
  0=colorless well or slightly bluish
  1+=well of a light blue color
  2+=well of a blue color
  3+=well of a dark blue color
  4+=well of a dark blue color The reading with a spectrophotometer was effected and calculated as described in section 8a above.

Specificity and Sensitivity of the Kit

The specificity of the kit of the present invention comes from a purified lipopolysaccharide antigen from a reference strain of A. pleuropneumoniae serotype 1. The kit allows for the detection of anti-A. pleuropneumoniae antibodies in the serum of pigs and to determine whether or not the pigs have developed antibodies. During an analysis, several animals of a herd must be verified to determine the status of the herd. The presence of at least one positive serum means that at least one A. pleuropneumoniae serotypes 1, 9 or 11 is present in the herd. When all the sera analyzed are negative, and if the sampling is representative of the herd, this indicates that the pigs analyzed have not developed antibodies against A. pleuropneumoniae serotypes 1, 9 or 11 and that during the blood sampling, the herd has not come in contact with the bacteria. Nevertheless, due to the limit of the serological testing, it is recommended to repeat the testing after a few weeks, the more analysis are negatives higher is the probability that the herd is free of A. pleuropneumoniae serotypes 1, 9 or 1. Following a first series of analysis, in cases where only weak positive and negative sera are observed, no status can be certified. It is then recommended to repeat the testing and to compare the results with those of a reference laboratory.

Firstly, the antigen specificity was verified using serum of pigs infected experimentally with strains of A. pleuropneumoniae of different serotypes or other bacteria. The ELISA method was used with ABTS as a chromogen. The antigen gave positive reactions with antisera against A. pleuropneumoniae serotypes 1, 9 and 11 and negative reactions for serotypes 2, 3, 4, 5 and 7. The sera from pigs inoculated with a strain of different serotypes of Actinobacillus pleuropneumoniae, Haemophilus parasuis, Pasteurella multocida, Escherichia coli, or A. suis gave negative results with the purified antigen. The results are presented in Table 2.

TABLE 2

ELISA results of the purified antigen A. pleuropneumoniae serotype 1 (strain 4074) against different sera of pigs inoculated experimentally

| Sera from pigs inoculated with | Optical density |
|---|---|
| A. pleuropneumoniae serotype 1 (strain Shoe 4074) | 0.69 |
| A. pleuropneumoniae serotype 2 (strain 4226) | 0.03 |
| A. pleuropneumoniae serotype 3 (strain 1421) | 0.01 |
| A. pleuropneumaniae serotype 3 (strain 89-92A13) | 0.04 |
| A. pleuropneumoniae serotype 4 (strain M62) | 0.04 |
| A. pleuropneumoniae serotype 5 (strain K17) | 0.05 |
| A. pleuropneumoniae serotype 7 (strain WF83) | 0.02 |
| A. pleuropneumoniae serotype 9 (strain CVJ 13261) | 0.58 |
| A. pleuropneumoniae serotype 11 (strain 56153) | 0.87 |
| Actinobacillus suis | 0.02 |
| Haemophilus parasuis | 0.02 |
| Pasteurella multicida | 0.02 |
| Escherichia coli | 0.02 |

Secondly, the plates were treated with HRP conjugate stabilizing solution after the sensitization with the antigen and the ELISA-TMBLue™ technique was used (Table 3).

TABLE 3

ELISA-TMBLue ™ results of the purified antigen A. pleuropneumoniae serotype 1 (strain 4074) against reference sera

| Serum used | Optical density | Visual Response |
|---|---|---|
| CN | 0.063 | 0 |
| CP | 1.884 | 3+ |
| EP1 | 2.097 | 4+ |
| EP2 | 0.995 | 2+ |
| EN1 | 0.139 | 0 |
| EN2 | 0.046 | 0 |
| ED1 | 0.515 | 1+ |
| ED2 | 0.450 | 1+ |

The CP, EP1 and EP2 sera gave positive responses. The serum CP came from a pool of sera obtained pursuant to the inoculation of two five weeks old piglets with the reference strain of A. pleuropneumoniae. The EP1 and EP2 sera were obtained from animals of a herd where clinical cases caused by A. pleuropneumoniae serotype 1 is frequently observed. The CN serum is the negative control serum which came from a pool of sera of a herd specific pathogen free where no history of A. pleuropneumoniae was ever reported for this herd since at least four years. The EN1 and EN2 sera came from two pigs from a herd of no history of A. pleuropneumoniae and lesions at the slaughter. These sera give a negative response in an ELISA. The ED1 and ED2 sera give weak positive responses in an ELISA. These sera came from two pigs from a herd chronically infected with A. pleuropneumoniae serotype 1.

Stability of the Kit

During the preliminary trials, different techniques of antigen attachment, different buffers, as well as different methods of preservation of the plates were evaluated. The preferred method with regard to the antigen attachment consists of diluting 150 µl of antigen in 75 ml of PBS-EDTA buffer, pH 7.3. 100 µl of this solution are then distributed in each well of the 96-well plates (Nunc™). The contents of the plates are incubated 18 hours at 4° C. Then the plates are washed three times with PBS-TWEEN™ −20 buffer. The contents of the plates are emptied and 100 µl of HRP conjugate stabilizing solution is added to each well. The plates are kept at 4° C. In addition to the three controls included in the kit, eight additional sera are used for the stability study of the kit. These additional sera are kept at −20° C. and a new aliquot is used for each assay. During each assay, a complete kit is used. The kit is validated with the different controls included in each kit. As shown in Table 4, the kit is stable for at least 25 weeks.

TABLE 4

Stability of the kit A. pleuropneumoniae serotype 1, 9 and 11 visual test

| | Number of weeks at 4° C. | | | | | |
|---|---|---|---|---|---|---|
| Sera | 0 | 4 | 7 | 12 | 20 | 25 |
| Positives (4+,3+,2+) | 5* | 5 | 5 | 5 | 5 | 5 |
| Weak positives (1+) | 1 | 1 | 1 | 1 | 1 | 1 |
| Negatives (0+) | 5 | 5 | 5 | 5 | 5 | 5 |

*Number of sera

Reproducibility of the Kit Depending on the User

Three complete kit were prepared. A total of 20 different sera obtained from the serology laboratory of the Veterinary Medicine Faculty of University of Montreal, a kit as well as an aliquot of each serum undiluted were given to three different user. Identical results were obtained by all of these users (Table 5).

TABLE 5

Evaluation of the kit A. pleuropneumoniae serotype 1, 9 and 11 visual test by three different users

| | batch | | |
|---|---|---|---|
| Sera | User #1 | User #2 | User #3 |
| Positives (4+,3+,2+) | 6* | 5 | 6 |
| Weak positives (1+) | 1 | 2 | 2 |
| Negatives (0+) | 16 | 16 | 15 |

*Number of sera

Finally in order to verify the sensitivity and the specificity of the kit of the present invention, several complete kits were prepared in three different batches. Each batch of kits was used with different sera (Table 6). A total of 295 sera, the status of which was determined by the pleuropneumonia serology laboratory of the Veterinary Medicine Faculty of the University of Montreal, were evaluated. The 192 negative sera classified as negative by the pleuropneumonia serology laboratory were confirmed as negative with the kit of the present invention. Within the sera classified as positive by the pleuropneumonia serology laboratory, 15 sera gave a 1+ response and the remaining 88 sera gave a 2–4+ response with the kit of the present invention (Table 6).

TABLE 6

Sensitivity and specificity of the kit
A. pleuropneumoniae serotype 1, 9 and
11 visual test during three different assays

| Results with the kit | Results with the "golden test" | |
|---|---|---|
| | Positive | Negative |
| 4–3+ | 45 | 0 |
| 2+ | 43 | 0 |
| 1+ | 15 | 0 |
| 0 | 0 | 192 |

Discussion

The determination of the sensitivity and the specificity of a test is effected either by using animal populations of status clearly identified as "infected" or as "healthy" or by comparing the test results with a reference test or a test referred to as a "golden" test. In accordance with the present invention, the two methods were used. As sera of well defined status, 13 sera from pigs infected experimentally with strains of A. pleuropneumoniae of different serotypes or with different bacteria were used. Thereafter, eight additional sera of pigs with well defined status were used; a serum from a pig infected experimentally with A. pleuropneumoniae serotype 1, a serum from a pool of sera of specific pathogen free pigs and six sera of pigs from different herds with a well defined status.

The ELISA kit of the present invention gave a positive response only with sera from pigs infected experimentally or naturally with A. pleuropneumoniae serotype 1, serotype 9 or serotype 11. The ELISA kit of the present invention gave negative results for sera of pigs infected experimentally with A. pleuropneumoniae serotypes 2, 3, 4, 5 and 7, H. parasuis, P. multicida, E. coli, or A. suis as well as for two pool of sera from pigs of specific pathogen free herds. The ED1 and ED2 sera came from pigs with no clinical signs of pleuropneumonia but where evidence of infection with A. pleuropneumoniae serotype 1 was reported for this herd. These sera gave a positive response with the kit of the present invention. The EN1 and EN2 sera which came from a herd with no history of pleuropneumonia, were considered as negative.

The ELISA kit of the present invention is stable at 4° C. for at least 25 weeks. The stability study is still in progress.

The pleuropneumonia laboratory was considered as the "golden test" and the positive limit was established so that a maximum of correlation between the two tests is obtained. This pleuropneumonia laboratory analyzes between 30,000 and 40,000 sera of pigs per year and this since more than 12 years. The method used by this laboratory consists in a standardized ELISA technique to determine the presence of antibodies, which method was established by comparing different antigens (Gottschalk, M. et al., 1994, Vet. Microbiol., 42:91–104). This laboratory has stopped using the complement fixation test due to its lack of sensitivity and specificity. Since this laboratory receives numerous serum samples, the results obtained by this laboratory were considered as a reference. The status of the sera, negative or positive, obtained by this laboratory was thus well certified. The specificity and the sensitivity of the kit was evaluated using 295 pig sera. A correlation of 100% was obtained. All the sera classified as negative by the reference serology laboratory were also determined as negative by the kit of the present invention. All the sera classified as positive by the reference laboratory were also confirmed as positive using the kit of the present invention.

The kit of the present invention differs from the ELISA method used by the reference serology laboratory. For the reference serology method, the antigen is fixed to the plates in a PBS buffer and the plates are immediately used after the antigen fixation is completed. This reference serology laboratory utilizes a computerized reading protocol for the determination of the antibodies in the samples (Trottier, Y. L. et al., 1992, J. Clin. Microbiol., 30:46–53). The kit of the present invention differs in that the antigen is purified using a higher concentration of phenol and the antigen fixation is different. Indeed, the purified antigen is resuspended in a PBS-EDTA buffer which is then added to each well of the plate. After an 18 hour incubation, HRP conjugate stabilizing solution is added to each well. The antibodies in the samples are then determined visually by adding a chromogen, preferably TMBlue™.

The kit of the present invention, when compared to the standardized ELISA method, demonstrate a relative sensitivity and a relative specificity of 100%. The kit of the present invention is faster to use than the ELISA-ABTS method of the prior art. The determination of A. pleuropneumoniae serotypes 1, 9 or 11 antibodies using the kit of the present invention can be effected in less than one hour whereas a minimum of three hours should is required for the ELISA-ABTS method in addition to one night of incubation for the antigen attachment step. Further, ABTS is considered as a potentially carcinogenic and has very little stability.

The kit of the present invention is easily used and provide rapid results. The kit of the present invention may be used in the field where the animals are kept and do not require laboratory skills since only simple steps are performed. This kit was demonstrated to give highly reliable and reproducible results and this independently of the users. The results obtained for the A. pleuropneumoniae serotypes 1, 9 and 11 samples are equivalent to the results obtained by the pleuropneumonia laboratory. The kit of the present invention is highly advantageous compared to the now available laboratory test with respect to its rapidity, reliability, sensitivity, specificity, stability and cost.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

Testing Alternative Options for Stabilizing the Antigen

That the following different options were tested to stabilize the antigen coated to the plates in accordance with the present invention.

a) Antigen Without Any Agent for the Stabilization Sensitization of the Plates:

Dilute the antigen in PBS-EDTA buffer, pH 7.3 to reach the appropriate concentration.

Add 100 µl of antigen to each well.

Seal the plate with an acetate sheet.

Incubate overnight at 4° C.

Results

Plates kept at 22° C. and 37° C.:

The reaction disappeared after 1–2 days.

Plates kept at 4° C.:

The reaction is significantly weaker after 14 days b) Antigen Stabilized with SPGA (Added Concurrently With Coating of the Antigen)
Sensitization of the Plates
  Dilute the antigen in SPGA buffer, pH 7.3 to reach the appropriate concentration. Mixtures of PBS-EDTA with SPGA (1:1, 1:0.5 and 1:0.25) were also tested.
  Add 100 μl of antigen to each well.
  Seal the plate with an acetate sheet.
  Incubate overnight at 4° C.
SPGA
  0.218 M sucrose
  0.0038 M monopotassium phosphate
  0.0049 M monosodium glutamate
  1% BSA (bovine serum albumin)
Results
  The SPGA competes with the antigen, thus NO positive reaction was obtained.
c) Antigen Stabilized With SPGA (Added 24 Hours After Coating With the Antigen)
Sensitization of the Plates
  Dilute the antigen in PBS-EDTA buffer, pH 7.3 to reach the appropriate concentration.
  Add 100 μl of antigen to each well.
  Seal the plate with an acetate sheet.
  Incubate overnight at 4° C.
  The content of the wells are emptied and 100 μl of SPGA is added to each well.
SPGA
  same as for b) above
Results
  The positive reaction dropped in plates kept at any temperature after 7 days. Non-specific background is very high.
d) Antigen Fixed Under Vacuum
Sensitization of the Plates
  Dilute the antigen in PBS-EDTA buffer, pH 7.3 to reach the appropriate concentration.
  Add 100 μl of antigen to each well.
  Seal the plate with an acetate sheet.
  Incubate overnight at 4° C.
  A complete vacuum of the plate is carried out.
Results
  The positive results are weaker at day 12 in plates kept at 4° C. High variability intra-plate (between wells). Low repeatability.
e) Antigen Fixed in Nitrogen
Sensitization of the Plates
  Dilute the antigen in PBS-EDTA buffer, pH 7.3 to reach the appropriate concentration.
  Add 100 μl of antigen to each well.
  Seal the plate with an acetate sheet.
  Incubate overnight at 4° C.
  A vacuum of the plate is carried out.
  The atmosphere is replaced by nitrogen.
Results
  Similar results to those obtained in d) above.
f) Antigen Fixed by Lyophilization
Sensitization of the Plates
  Dilute the antigen in PBS-EDTA buffer, pH 7.3 to reach the appropriate concentration.
  Add 100 μl of antigen to each well.
  Seal the plate with an acetate sheet.
  Incubate overnight at 4° C.
  The antigen is lyophilized directly on the plate.
Results
  The positive results are weaker at day 12 in plates kept at 4° C.
  Similar results to those obtained in d) and e) above.
g) Plates Kept at −20° C.
Sensitization of the Plates
  Dilute the antigen in PBS-EDTA buffer, pH 7.3 to reach the appropriate concentration.
  Add 100 μl of antigen to each well.
  Seal the plate with an acetate sheet.
  Incubate overnight at 4° C.
  The plates are kept at −20° C.
Results
  The positive reaction is weaker after 14 days. High variability among different wells.
h) HRP Stabilization Reactive (Added Concurrently With the Coating of the Antigen)
Sensitization of the Plates
  Dilute the antigen in HRP conjugate stabilizing solution to reach the appropriate concentration.
  Add 100 μl of antigen to each well.
  Seal the plate with an acetate sheet.
  Incubate overnight at 4° C.
Results
  The HRP stabilization reactive competes with the antigen, thus NO positive reaction was obtained.
i). HRP Stabilization Reactive (Added 24 Hours After Coating With the Antigen)
Sensitization of the Plates
  Dilute the antigen in PBS-EDTA buffer, pH 7.3 to reach the appropriate concentration.
  Add 100 μl of antigen to each well.
  Seal the plate with an acetate sheet.
  Incubate overnight at 4° C.
  The content of the wells are emptied and 100 μl of HRP conjugate stabilizing solution is added to each well.
Results
  The plates keep the active antigen and good reproducibility at different temperatures (4° C., 22° C. and 37° C.).
  At 4° C., plates can be kept for at least 9 months without any change in optical densities obtained by ELISA. This was the procedure chosen to prepare the plates of the present invention.

We claim:

1. An ELISA diagnostic kit for the assay of A. pleuropneumoniae serotypes 1, 9 or 11 antibodies in the serum of pigs comprising in separate packaging:
  a) a solid support having bound thereto a purified lipopolysaccharide A. pleuropneumoniae serotype 1 unreacted antigen for a specific binding to anti-A. pleuropneumoniae serotypes 1, 9 or 11 antibodies present in the serum of pigs, wherein the bound antigen is stored in phosphate buffered saline pH 7.2, containing BSA, 0.1% thimerosal and caprylic acid, which keeps said bound antigen stable for at least 25 weeks at 4° C.; and
  b) a detectably labeled conjugate which binds to said antibodies.

2. The kit of claim 1, which further comprises a substrate which allows the visualization of the detectably labeled conjugate.

3. The kit of claim 2, wherein said detectably labeled conjugate comprises an enzyme label.

4. The kit of claim 3, wherein said substrate is a composition which provides a colorimetric, fluorimetric, or chemiluminescent signal in the presence of said enzyme label.

5. The kit of claim 3, wherein said detectably labeled conjugate comprises pig anti-IgG immunoglobulins coupled to peroxidase.

6. The kit of claim 4, wherein said composition is 3,3',5,5'-tetramethylbenzidine.

7. The kit of claim 1 further comprising at least one package of
serum from pigs experimentally inoculated with a strain a A. pleuropneumoniae serotype 1 to serve as a positive control.

8. The kit of claim 7 further comprising at least one package of
pig serum from a specific pathogen free herd to serve as a negative control.

9. The kit of claim 1, wherein said solid support is a 96-well plate.

10. The kit of claim 8, wherein any of said positive or negative control serum is lyophilized serum.

11. The kit of claim 10, wherein any of said positive or negative control serum is in the amount of about 0.1 ml of lyophilized serum.

12. An ELISA diagnostic kit for the assay of A. pleuropneumoniae serotypes 1, 9 or 11 antibodies in the serum of pigs comprising in separate packaging:
   a) a plate having bound thereto a purified lipopolysaccharide A. pleuropneumoniae serotype 1 unreacted antigen for a specific binding to anti-A. pleuropneumoniae serotypes 1, 9 or 11 antibodies present in the serum of pigs, wherein the bound antigen is stored in phosphate buffered saline pH 7.2, containing BSA, 0.1% thimerosal and caprylic acid, which keeps said bound antigen stable for at least 25 weeks at 4° C.;
   b) a positive control vial of serum from pigs experimentally inoculated with a strain of A. pleuropneumoniae serotypes 1, 9 or 11;
   c) a negative control vial of pig serum from A. pleuropneumoniae free herd;
   d) a weak positive control vial of serum from pigs experimentally inoculated with a strain of A. pleuropneumoniae serotypes 1, 9 or 11;
   e) a conjugate vial of pig anti-IgG immunoglobulins coupled to peroxidase; and
   f) a colorimetric composition consisting of 3,3',5,5'-tetramethylbenzidine or 2,2-azino-bis(3-ethylbenthiazoline-6-sulfonic acid).

13. A method for the preparation of the kit of claim 12, which comprises the steps of:
   a) purifying lipopolysaccharide A. pleuropneumoniae serotype 1 antigen by phenol extraction and centrifugation of said antigen bacterial crude extract;
   b) fixing the antigen of step a) to a solid support and stabilizing said fixed antigen by storing it in phosphate buffered saline pH 7.2, containing BSA, 0.1% thimerosal and caprylic acid, which keeps the fixed antigen stable for at least 25 weeks at 4° C.;
   c) immunizing mammals with a strain of A. pleuropneumoniae serotype 1 and collecting serum to serve as positive control sera; and
   d) collecting sera from A. pleuropneumoniae free herds to serve as negative control sera.

14. A solid support for use in an assay of A. pleuropneumoniae serotype 1, 9 and 11 antibodies in the serum of pigs having bound thereto a purified lipopolysaccharide A. pleuropneumoniae serotype 1 unreacted antigen for a specific binding to anti-A. pleuropneumoniae serotypes 1, 9 or 11 antibodies present in the serum of pigs, wherein the bound antigen is stored in phosphate buffered saline pH 7.2, containing BSA, 0.1% thimerosal and caprylic acid, which keeps said bound antigen stable for at least 25 weeks at 4° C.

15. The kit of claim 14, wherein said solid support is a 96-well plate.

* * * * *

UNITED STATES PATENT AND TRADEMARK OFFICE
CERTIFICATE OF CORRECTION

PATENT NO.   : 6,218,195 B1
DATED        : April 17, 2001
INVENTOR(S)  : Marcelo Gottschalk, Daniel Dubreuil and Real Lallier It is certified that error appears in the above-identified patent and that said Letters Patent is hereby corrected as shown below:

Column 4,
Line 42, please change the word "9203C" to read -- 92039 --;
Line 47, please change the word "o" to read -- of --;
Line 62, please change the word "pigs" to read -- pig --;

Columns 9 and 10,
Table 1, Column 1 entitled "Serum", please change the word "ENI" to read -- EN1 --;
Table 1, Column 1 entitled "Serum", please change the word "EDI" to read -- ED1 --.

Column 10,
Line 58, please change the words "1, 9 or 1" to read -- 1, 9, or 11 --;

Column 11,
Line 62, please change the words "trial,different" to read -- trials, different --;

Column 13,
Line 34, please change the word "pool" to read -- pools --;

Column 14,
Line 22, please change the word "is" to read -- be --;
Line 67, please change the word "days" to read -- days. --;

Column 16,
Line 30, please change the word "i)." to read -- i) --.

Signed and Sealed this

Twenty-fifth Day of June, 2002

Attest:

Attesting Officer

JAMES E. ROGAN
Director of the United States Patent and Trademark Office